United States Patent [19]

Yamasaki et al.

[11] Patent Number: 5,631,397
[45] Date of Patent: May 20, 1997

[54] PROCESS FOR PRODUCING OPTICALLY ACTIVE DIAMINOHEXANONE DERIVATIVE

[75] Inventors: Tetsuro Yamasaki; Hidenori Kumobayashi; Noboru Sayo; Toshiyuki Murayama; Noboru Sano; Takero Ishizaki, all of Hiratsuka, Japan

[73] Assignee: Takasago International Corporation, Tokyo, Japan

[21] Appl. No.: 470,466

[22] Filed: Jun. 6, 1995

Related U.S. Application Data

[62] Division of Ser. No. 229,678, Apr. 19, 1994, Pat. No. 5,523,458.

[30] Foreign Application Priority Data

Mar. 17, 1994 [JP] Japan ................. 6-47182

[51] Int. Cl.$^6$ .................. C07C 269/06; C07C 231/12
[52] U.S. Cl. ................. 560/27; 564/161; 564/212; 564/220
[58] Field of Search ............... 560/27; 564/161, 564/212, 220

[56] References Cited

U.S. PATENT DOCUMENTS 5,523,458  6/1996  Yamasaki et al. ............ 560/27

*Primary Examiner*—Richard L. Raymond
*Attorney, Agent, or Firm*—Oblon, Spivak, McClelland, Maier & Neustadt, P.C.

[57] ABSTRACT

Disclosed herein is a process for producing a (2S,5S)-2,5-diamino-1,6-diphenyl-3-hexanone derivative represented by the formula (1):

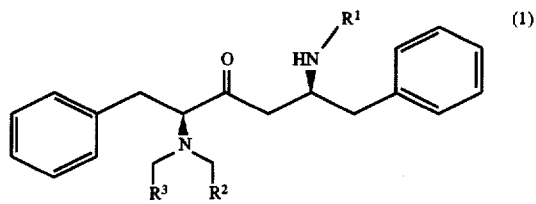

wherein $R^1$ means a lower alkylcarbonyl group, a halogen-substituted lower alkylcarbonyl group, an arylcarbonyl group or a lower alkoxycarbonyl group, and $R^2$ and $R^3$ are identical with or different from each other and denote individually an aryl group or an alkoxy-substituted aryl group, which comprises subjecting a (2S)-2,5-diamino-1,6-diphenyl-4-hexen-3-one derivative represented by the formula (2):

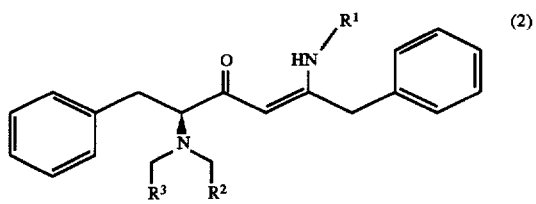

wherein $R^1$, $R^2$ and $R^3$ have the same meaning as defined above, to a hydrogenation reaction in the presence of a transition metal-containing catalyst.

10 Claims, No Drawings

PROCESS FOR PRODUCING OPTICALLY ACTIVE DIAMINOHEXANONE DERIVATIVE

This is a Division of application Ser. No. 08/229,678, filed on Apr. 19, 1994, now U.S. Pat. No. 5,523,458.

BACKGROUND OF THE INVENTION

1. Field of the Invention

The present invention relates to a process for producing an optically active 2,5-diamino-1,6-diphenyl-3-hexanone derivative, and more particularly to a process for producing an intermediate for a compound represented by the formula (9):

A-X-B (9)

wherein X means the formula (10):

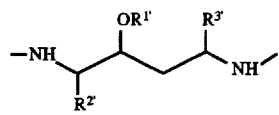

in which $R^{1'}$ is a hydrogen atom or a lower alkyl group, and $R^{2'}$ and $R^{3'}$ are, independently, an arylalkyl group or a cycloalkylalkyl group, and A and B denote $R^{6'}$—C(O)—(NH)— (CH($R^{5'}$))—(CO)— and $R^{6'}$—C(O)—, in which $R^{6'}$ is $R^{7'}$—NH—, $R^{7'}$—N(lower alkyl)— [$R^{7'}$ being a (heterocyclic ring)alkyl group], and $R^{5'}$ is a lower alkyl group, said compound inhibiting retrovirus proteases, in particular, HIV proteases participating in the proliferation and expression of characters of human immunodeficiency viruses (HIV), and pharmaceutically permissible salts thereof or prodrugs (Japanese Patent Application Laid-Open No. 308574/1992).

2. Description of the Background Art

The compound represented by the plane formula (11):

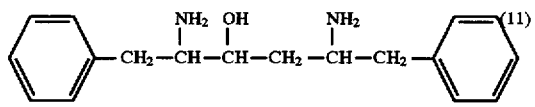

which is an intermediate for a compound having an HIV protease inhibitory action has eight optical isomers attributable to the three asymmetric carbon atoms. Of these, only a substance derived from (2S,3S,5S)-2,5-diamino-1,6-diphenyl-3-hexanol represented by the formula (12):

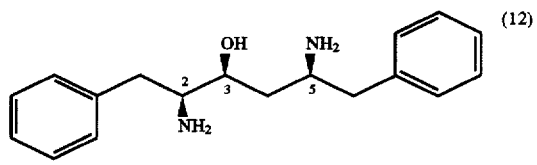

exhibits an anti-HIV protease activity, and those derived from other optical isomers substantially have no anti-HIV protease activity. In order to efficiently synthesize the intended compound exhibiting the anti-HIV protease activity, it is therefore necessary to establish a process for efficiently synthesizing either the compound having the (2S,3S,5S) configuration and represented by the formula (12), or an intermediate therefor.

As examples of the process for synthesizing the compound (12), have been known the process reported by Gaush et al. [J. Org. Chem., 58, 1025 (1993)], the process reported by Kemp et al. (Japanese Patent Application Laid-Open No. 308574/1992), and the like.

Besides, the compound (12) is obtained by incorporating 4 hydrogen atoms into the double bond and the ketone group in an optically active compound represented by the formula (13):

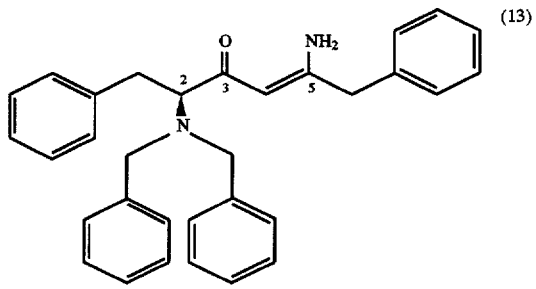

and eliminating the protective benzyl groups therefrom. However, 4 isomers based on the asymmetric carbon atoms situated at the 3- and 5-positions are formed according to a common process. Further, there has been proposed a process in which the compound (13) is treated with excess amounts of sodium borohydride and an acid to derive a compound represented by the formula (14):

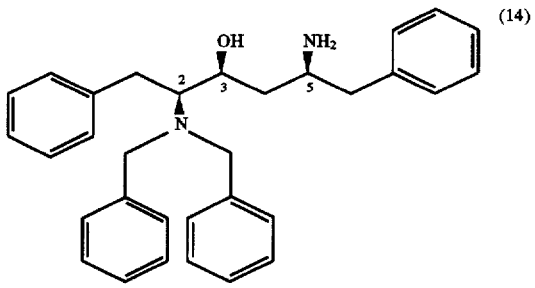

and the compound (14) is catalytically reduced to eliminate the protective benzyl groups, thereby producing the compound (12). However, this process involves a disadvantage that it is unfit for mass production because the purity of the above product and the yield of the intended compound are low, an expensive reagent must be used in a great amount, and a great amount of waste liquor is discharged.

SUMMARY OF THE INVENTION

It is thus an object of the present invention to provide a process for stereoselectively and efficiently producing a (2S,5S)-2,5-diamino-1,6-diphenyl-3-hexanone derivative, which is an intermediates for the compound (12) which is high in utility value as an intermediate of pharmaceutical for treatment of acquired immunodeficiency syndrome (AIDS), and represented by the formula (1):

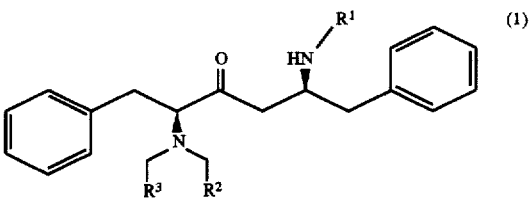

wherein $R^1$ means a lower alkylcarbonyl group, a halogen-substituted lower alkylcarbonyl group, an arylcarbonyl group or a lower alkoxycarbonyl group, and $R^2$ and $R^3$ are identical with or different from each other and denote individually an aryl group or an alkoxy-substituted aryl group.

In view of the foregoing circumstances, the present inventors have carried out an extensive investigation as to a process for efficiently and stereoselectively producing the compound (12) or a precursor thereof. As a result, it has been found that instead of direct hydrogenation of the compound (13), when the compound (2) obtained by introducing a protective group into the 5-amino group in the compound (13) is hydrogenated in the presence of a transition metal-containing catalyst, the compound (1) [(2S,5S) isomer] can be produced stereoselectively and efficiently, thus leading to completion of the present invention.

In an aspect of the present invention, there is thus provided a process for producing a (2S,5S)-2,5-diamino-1,6-diphenyl-3-hexanone derivative represented by the formula (1):

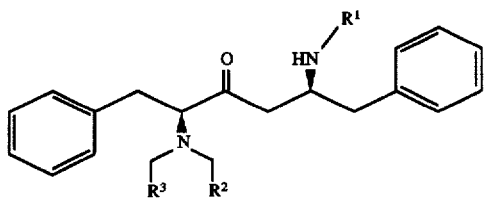

wherein $R^1$, $R^2$ and $R^3$ have the same meaning as defined above, which comprises subjecting a (2S)-2,5-diamino-1,6-diphenyl-4-hexen-3-one derivative represented by the formula (2):

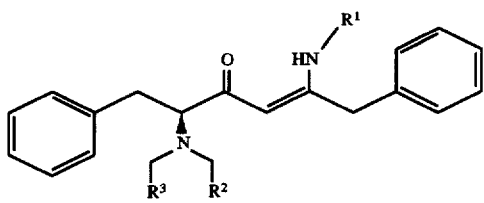

wherein $R^1$, $R^2$ and $R^3$ have the same meaning as defined above, to a hydrogenation reaction in the presence of a transition metal-containing catalyst.

According to the present invention, (2S,5S)-2,5-diamino-1,6-diphenyl-3-hexanone derivatives, which are intermediates of pharmaceuticals useful for treatment of AIDS, can be produced stereoselectively and efficiently.

The above and other objects, features and advantages of the present invention will become apparent from the following description and the appended claims.

DETAILED DESCRIPTION OF THE INVENTION AND PREFERRED EMBODIMENTS

The process according to the present invention is expressed by the following reaction scheme:

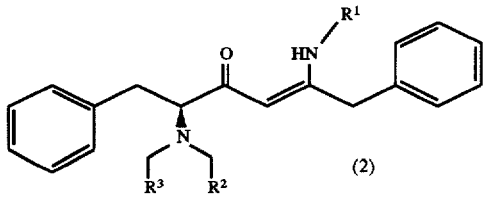

-continued

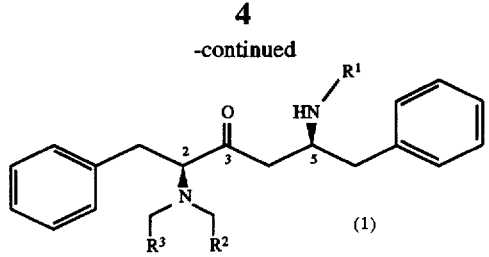

wherein $R^1$, $R^2$ and $R^3$ have the same meaning as defined above.

The compound represented by the formula (2), which is a starting material in the process of the present invention, is produced by reacting a compound represented by the formula (16) with an acylating agent represented by the formula (17) in accordance with, for example, the following reaction scheme:

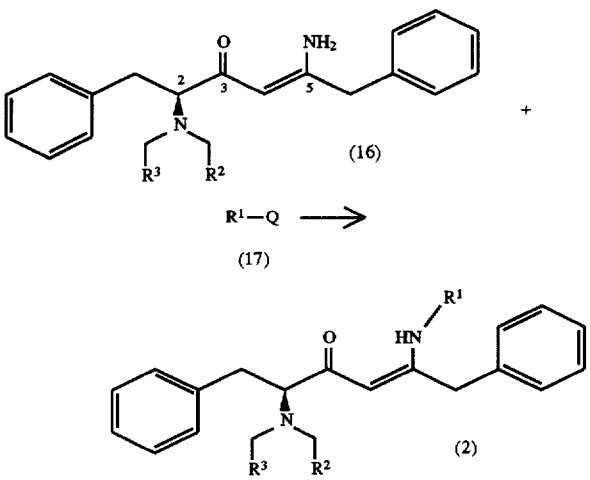

wherein Q means a carboxylic active group, and $R^1$, $R^2$ and $R^3$ have the same meaning as defined above.

In the above reaction scheme, Q is preferably a halogen atom (carboxylic acid halide) or an acyloxy group (acid anhydride). This acylation is preferably performed in the presence of a base such as pyridine, 4-dimethylaminopyridine, dimethylaniline, sodium carbonate or sodium acetate.

In the above reaction scheme, examples of the lower alkylcarbonyl group indicated by $R^1$ include linear or branched alkylcarbonyl groups having 2-7 carbon atoms. Specific examples thereof include acetyl, propionyl, butyryl, isobutyryl, valeryl, isovaleryl, pivaloyl, 3-methylpentanoyl and 4-methylpentanoyl groups. Specific examples of the arylcarbonyl group include benzoyl, naphthoyl, methylbenzoyl and dimethylbenzoyl groups. Examples of the lower alkoxycarbonyl group include alkoxycarbonyl groups having 2-7 carbon atoms. Specific examples thereof include methoxycarbonyl, ethoxycarbonyl, n-propoxycarbonyl, isopropoxycarbonyl, n-butoxycarbonyl, t-butoxycarbonyl, t-amyloxycarbonyl and n-hexyloxycarbonyl groups. Specific examples of the aryl groups indicated by $R^2$ and $R^3$ include phenyl, naphthyl, tolyl and xylyl groups. Examples of the alkoxy-substituted aryl groups include aryl groups substituted with 1-3 alkoxy groups having 1-6 carbon atoms.

The compound represented by the formula (2) is expressed as the formula (18):

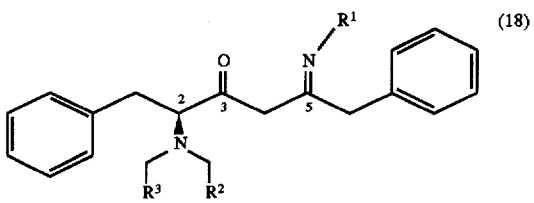
(18)

wherein $R^1$, $R^2$ and $R^3$ have the same meaning as defined above, which are expressed as an imido form of an imido-enamido equilibrium mixture and are substantially equivalent to the compound of the formula (2).

That is, the compound represented by the formula (2) includes either of the two compounds which are substantially equivalent to formula (2) or a mixture of the two in an arbitrary proportion.

The catalyst in the hydrogenation reaction according to the present invention is a transition metal-containing catalyst. Examples of the transition metal used in the present invention include titanium, chromium, manganese, iron, cobalt, nickel, copper, ruthenium, rhodium, palladium, rhenium, osmium, iridium and platinum. Of these, ruthenium, rhodium, palladium and iridium are preferred, with iridium, rhodium and palladium being more preferred.

These metals may be used as catalysts in the form of metal catalysts being in an activated state. As specific examples thereof, may be mentioned Raney nickel, platinum oxide, platinum black, palladium black and rhodium black. More preferable examples thereof include palladium black and rhodium black.

They may also be used as metal catalysts supported on various supports. As supports on which these metals are supported, any support may be used so far as it does not inhibit the reaction. However, the activity, regio- and stereoselectivity of the reaction may be greatly affected according to the kind and quality of supports, and the production process of catalysts.

Specific examples of supports usable in the present invention include active carbon, alumina, silica, silica-alumina, zeolite, titania, zirconia, magnesia, mordenite, montmorillonite, mica, aluminum phosphate, silicon tetrafluoride, silicon carbide, calcium carbonate, barium carbonate, calcium sulfate and the like. Preferred examples thereof include active carbon, alumina, silica and silica-alumina, with alumina and silica-alumina being more preferred. These supports may be used either by itself or in any combination thereof. With respect to processes for supporting the transition metal on these supports to produce metal catalysts, those skilled in the art can easily come to know them. Most of these catalysts may also be purchased from makers. A proportion of the metal to the support is preferably within a range of 0.1–30% by weight, particularly 1–20% by weight.

These metals may be used in the form of a solution as organometallic complex catalysts.

The hydrogenation reaction making use of the organometallic complex catalyst is performed in the thermodynamic equilibrium of all components participating in the reaction under reaction conditions. Actual active species of the catalysts may be different from the compositions upon preparation in some cases. As an example thereof, may be mentioned a hydride type catalyst in which a catalyst composition is hydrogenated in advance without adding a reaction substrate to introduce a hydrogen atom as a component in an activated catalyst before its use. It is also said that the actual active species in many catalysts are formed under conditions for a reducing reaction. The structures of the actual active species in the catalysts have not been clarified yet in many cases. The organometallic complex catalysts will be described subsequently in detail.

As examples of the catalyst used in the present invention, may be mentioned catalysts prepared in accordance with the following preparation processes. No limitation is imposed on actual active species in catalytic reactions.

As a typical process for supporting these metal catalysts on supports, may be mentioned a process in which a solution of a metal salt or organometallic complex is supported on a solid support. More specifically, there may be used impregnation processes such as absorption process, pore-filling process, incipient wetness process, evaporation and dryness process and spray process; deposition processes such as coprecipitation process, sedimentation process and kneading process; and ion exchange processes. Besides, the precursor of catalyst, in which a metal oxide or hydroxide, metal salt, or organometallic complex has been supported on a solid support, may be washed and dried to isolate it. This catalyst precursor is activated to obtain a metal-containing catalyst supported on a support. As examples of the activation process, may be mentioned (a) reduction in a hydrogen atmosphere, (b) reduction with a hydride reagent such as sodium borohydride, (c) reduction with hydrogen generated upon decomposition of formaline or formic acid, and (d) thermal decomposition in the presence of inert gas or steam. Through this process, the metal is supported in the form of fine particles on the surface of the support to provide catalytic activity. The catalyst precursor may be used in hydrogenation reaction as it is. In this case, the precursor is activated under hydrogenation conditions.

Examples of the organometallic complex catalyst include mononuclear complexes represented by the formula (3):

$$M(L_n)(Y_p)(X_q) \quad (3)$$

wherein M is the same metal as described above, L denotes an organophosphorus compound, cyclopentadienyl group, pentamethylcyclopentadienyl group or hexamethylbenzene, Y stands for a co-ligand such as ethylene, 1,5-cyclooctadiene, norbornadiene, p-cymene, acetonitrile, benzonitrile, acetic acid, benzene, pyridine, quinoline or isoquinoline, X is a halogen ion, sulfonate ion, acetate ion, $ClO_4$, $BF_4$, $PF_6$ or the like, or X and Y form together a β-diketonate, n stands for a number of 1–3, and p and q are individually a number of 0–2, and binuclear complexes represented by the formula (4):

$$M_2(L_{2n})(Y_{2p})(X_{2q}) \quad (4)$$

wherein M, L, X, Y, n, p and q have the same meaning as defined above. Further, those obtained by adding an excessive amount of the ligand or a compound capable of undergoing addition, such as triethylamine to these catalysts may be included. Metal complex catalysts activated by reducing these catalysts may also be used.

As specific examples of the metal complexes [formula (3)] obtained in the above-described manner, may be mentioned the following complexes:

[M(L)($C_2H_4$)Cl],
[M(L)($C_2H_4$)Br],
[M(L)($C_2H_4$)F],
[M(L)($C_2H_4$)I],
[M(L)($C_2H_4$)CN],
[M(L)(cod)]Cl,
[M(L)(cod)]$BF_4$,

[M(L)(cod)]PF$_6$,
[M(L)(nbd)]ClO$_4$,
[M(L)(acac)],
[M(L)(pyridine)Cl], and
[M(L)(nbd)CH$_3$COO]
wherein cod means cyclooctadiene, nbd denotes norbornadiene, and acac stands for acetylacetone. Besides, it may be used those obtained by adding an excessive amount of the ligand (L) to these metal complexes, or by adding the ligand in an amount of 1–4 equivalent to the metal to a commercially-available complex.

Preferable examples of the organometallic complexes include the following complexes a), b) and c):

a) Organometallic complexes in which in the formula (3) or (4), the metal is rhodium, ruthenium or iridium, and the ligand (L) is an organophosphorus compound which is either a unidentate ligand represented by the formula (5):

P(R$^4$)$_3$ (5)

wherein R$^4$ means a lower alkyl group, a phenyl group or a tolyl group, or a bidentate ligand represented by the formula (6):

(R$^5$)$_2$P-A-P(R$^5$)$_2$ (6)

wherein R$^5$ means a lower alkyl group, a phenyl group or a tolyl group, and A denotes the formula (7):

(R$^6$)CH—(CH$_2$)$_m$—CH(R$^7$) (7)

in which R$^6$ and R$^7$ mean individually a hydrogen atom or a lower alkyl group, or R$^6$ and R$^7$ are bonded to each other to form a ring, and m stands for a number of 0–8.

Of the complexes a), specific examples of particularly preferred complexes include the following compounds:
RuCl$_2$(PPh$_3$)$_3$,
[Rh(cod)Ph$_2$P-(CH$_2$)$_2$-PPh$_2$]ClO$_4$,
[Rh(cod)Ph$_2$P-(CH$_2$)$_4$-PPh$_2$]ClO$_4$,
[Rh(cod)(Cy)$_2$P-(CH$_2$)$_2$-P(Cy)$_2$]ClO$_4$ and
[Ru$_2$Cl$_2$(Ph$_2$P-(CH$_2$)$_4$-PPh$_2$)$_2$](NEt$_3$)
wherein Ph, Cy and NEt$_3$ mean a phenyl group, a cyclohexyl group and a triethylamine, respectively.

b) Organometallic complexes in which in the formula (4), the metal is rhodium, ruthenium or iridium, and the ligand (L) is an optically active organophosphorus compound which has axial dissymmetry and is represented by the formula (19):

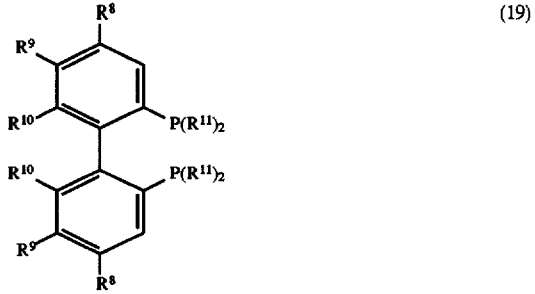

(19)

wherein R$^{11}$ means a phenyl group which may have a substituent group, R$^{10}$ is a methyl group, and R$^8$ and R$^9$ denote individually a hydrogen atom, a halogen atom or a lower alkyl group, with the proviso that R$^9$ and R$^{10}$ may form together a ring, or is an optically active organophosphorus compound which has asymmetry and is represented by the formula (20) or (21):

(20)

(21)

[the formula (20) and the formula (21) will hereinafter be abbreviated as "CHIRAPHOS" and "DIOP", respectively].

Particularly preferred compounds of the optically active organophosphorus compounds represented by the formula (19) are those represented by the following formula (22):

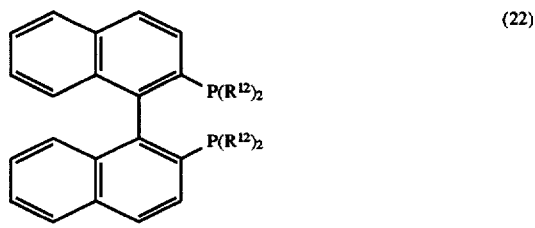

(22)

wherein R$^{12}$ means a phenyl group which may have a substituent group. The compound of the formula (22) is abbreviated as "BINAP" where R$^{12}$ is a phenyl group, and as "TolBINAP" where R$^{12}$ is a p-tolyl group.

Of these six kinds of the organophosphorus complexes in b), specific examples of particularly preferred compounds include the following compounds:
[Rh(cod)(S)-CHIRAPHOS]ClO$_4$,
[Rh(cod)(R)-TolBINAP]ClO$_4$,
[Ru$_2$Cl$_4$((R)-BINAP)$_2$](NEt)$_3$,
[Ru$_2$Cl$_4$((S)-BINAP)$_2$](NEt)$_3$,
[Ru(OAc)$_2$(S)-TolBINAP], and
[RuI(p-cymene)(R)-TolBINAP]I
wherein CHIRAPHOS, BINAP and TolBINAP have the same meaning as described above.

When such an optically active organophosphorus compound is used as a ligand, the stereoselectivity of the intended product is enhanced by the optically active organophosphorus ligand. As a specific example thereof, may be mentioned a case where the stereoselectivity is reversed as demonstrated by the fact that (2S,5S)/(2S,5R) is 87/13 when [Rh(cod)$_2$(2S,3S)-bis(diphenylphosphino)-butane]ClO$_4$ is used (Example 7–4), while (2S,5S)/(2S,5R) is 36/69 when [Rh(cod)$_2$(2R,3R)-bis(diphenylphosphino)-butane]ClO$_4$ is used (Example 7–5).

c) Organometallic complexes in which in the formula (3) or (4), the metal is rhodium, ruthenium or iridium, and the ligand (L) is an unsaturated hydrocarbon represented by the formula (23), (24) or (25):

(23)

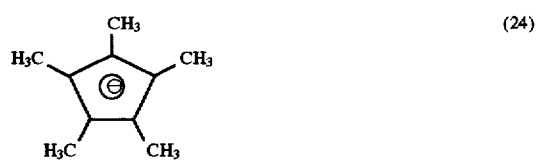

(24)

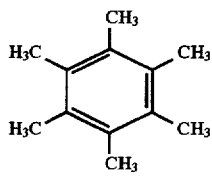

wherein the formulae (23), (24) and (25) are abbreviated as "Cp", "Cp*" and "C₆Me₆", respectively.

Of the complexes c), specific examples of particularly preferred complexes include the following compounds:

[RhCl₂Cp*]₂,
[RUCl₂Cp*]₂,
[RuCl₂(C₆Me₆)]₂,
[IrCl₂Cp*]₂,
[Rh(cod)Cp],
[Rh(cod)(C₆Me₆)]BF₄ and
[IrI₂Cp*]₂ wherein Cp, Cp*, C₆Me₆ have the same meaning as described above.

The hydrogenation reaction according to the present invention, more specifically, is conducted in the presence of a carrier-supported metal catalyst in a metal/substrate weight ratio of from 1/5 to 1/20,000, preferably from 1/20 to 1/2,000, or of an organometallic complex catalyst in a complex/substrate molar ratio of from 1/10 to 1/20,000, preferably from 1/200 to 1/2000, either in a hydrogen stream atmosphere or in the presence of a hydrogen source. Of the conditions for the reaction, the reaction temperature is preferably within a range of usually from −20° C. to 250° C., particularly from −20° C. to 100° C. Lower reaction temperatures are usually desirable herein from the standpoints of the thermal stability of the starting material and reaction product and the selectivity in the reaction, but higher reaction temperatures are preferred for increasing the reaction rate.

In the case where the hydrogenation reaction according to the present invention is conducted catalytically in a hydrogen stream, the hydrogen pressure is preferably within a range of from 1 to 200 atm, more preferably from 1 to 100 atm. The hydrogen may be diluted with other gas inactive in the reaction. Examples of gases usable as the diluent include methane, nitrogen, argon, helium, carbon dioxide and the like. These diluent gases may be used either by itself or in any combination thereof. On the other hand, in the case where the hydrogenation reaction is conducted by means of hydrogen transfer reaction in the presence of a metal catalyst, examples of the hydrogen source include alcohols, formic acid and salts thereof, hydrazine, hydride reagents and lower alkenyl compounds. As specific examples thereof, may be mentioned isopropanol, formic acid, ammonium formate, sodium borohydride, cyclohexene, cyclohexadiene and cyclooctadiene. This reaction is carried out in a solvent and, hence, if the hydrogen source is liquid, it may also be used as a reaction solvent.

Any solvent is able to be used for the reaction so long as it can dissolve the substrate and does not adversely affect the reaction. Specifically, the solvent may be selected from water; hydrocarbons such as hexane, heptane, octane, nonane, decane, benzene, toluene and xylene; ethers such as tetrahydrofuran, dioxane, dimethoxyethane, diisopropyl ether and diethylene glycol dimethyl ether; esters such as ethyl acetate, butyl acetate and ethyl propionate; ketones such as acetone, diisopropyl ketone, methyl isobutyl ketone, methyl ethyl ketone and acetylacetone; alcohols such as methanol, ethanol, n-propanol and isopropanol; nitriles such as acetonitrile; halogenated alkyls such as dichloromethane, chloroform and dichloroethane; amines such as triethylamine and diisobutylamine; and organic acids such as acetic acid and formic acid. In the case where an activated metal is used as it is or a metal is used after supported on a solid support, preferred examples of the solvent include alcohols such as methanol, ethanol and isopropanol; esters such as ethyl acetate; ethers such as tetrahydrofuran, dioxane, dimethoxyethane; and ketones such as acetone, methyl ethyl ketone, diisopropyl ketone and methyl isobutyl ketone, with ethyl acetate and acetone being particularly preferred. In the case where an organometallic complex is used as a catalyst, preferred examples of the solvent include methanol, ethanol, isopropanol, tetrahydrofuran and ethers. In the case where the reaction is carried out in the presence of a hydrogen source, isopropanol is preferred.

The activity, and regio- and stereoselectivity in the reaction are considerably affected depending upon the kind of the solvent. It is therefore necessary to give heed, in particular, to the combination of a metal catalyst and a solvent to be used. The solvents may be used either by itself or in any combination thereof. In some cases, an acid, a base or a substance which serves to enhance the activity of a catalyst or affect the selectivity in the reaction may be added to these solvents. Examples of such a substance include small amounts of mercaptans and silver salts.

The present invention will hereinafter be described in detail by reference to Reference Examples and Examples. However, it should be borne in mind that this invention is not limited to and by these examples only.

Incidentally, the physical properties that follow were measured under the following conditions.

Melting Point

Measurement was made with a hot stage type melting point apparatus manufactured by Yanagimoto Seisakusho, Japan, with no correction of the found values.

HPLC

Measurement of optical purity was made under the following conditions:

Column: COSMOSIL 5SL, 4.6×250 mm;

Mobile phase: hexane/THF=80/20–95/5;

Flow rate: 1.0 ml/min;

Detection: UV, 254 nm.

REFERENCE EXAMPLE 1

Synthesis of (2S,3S,5S)-2-(N,N-dibenzylamino)-5-acetyl-amino-1,6-diphenyl-3-hexanol (2S,5S)-2-(N,N-Dibenzylamino)-5-acetylamino-1,6-diphenyl-3-hexanone (3.0 g, 5.944 mmol) was dissolved in methanol (15 ml). Sodium borohydride (1.80 g, 23.78 mmol) was slowly added to the resultant solution while chilling with ice water so as not to raise the temperature above 10° C., thereby conducting reaction. The reaction mixture was stirred at room temperature for 5 hours. To the reaction mixture, was added a 10% hydrochloric acid (10 ml) while chilling with ice water. After bubbling ceased, the mixture was extracted with ethyl acetate (50 ml). The extract was washed with an aqueous sodium chloride and dried over sodium sulfate. The solvent was distilled off, and the resulting crude product was recrystallized from a mixed solvent of ethyl acetate (1.5 ml) and n-hexane (6 ml), thereby obtaining the title compound (2.70 g, 86.1%) as colorless crystals.

m.p. 84°–86° C.

[α]$_D^{24}$ +9.91° (C=1.00, CHCl$_3$)

IR (KBr, cm$^{-1}$) v: 3500, 3390, 3275, 1655.

$^1$H-NMR (400 MHz, CDCl$_3$) δ: 1.05–1.15(1H,m), 1.48–1.56(1H,m), 1.90(3H,s), 2.50–2.67(2H,m), 3.01–3.10 (1H,m), 3.38(2H,d, J=13.4 Hz), 3.52–3.60(1H,m), 3.88(2H, d,J=13.4 Hz), 3.99–4.01(1H,m), 4.54(1H,s), 5.98(1H,d,J= 6.7 Hz), 6.95–7.35 (20H,m).

REFERENCE EXAMPLE 2

Synthesis of (2S, 3S, 5S) -2-amino-5-acetylamino-1,6-diphenyl-3-hexanol

To a solution of 100 g of (2S,3S,5S)-2-(N,N-dibenzylamino)-5-acetylamino-1,6-diphenyl-3-hexanol in 500 ml of methanol, was added 5 g of 5%-palladium-carbon (product of N. E. Chemcat), and the reaction mixture was stirred at 30° C. for 30 hours under a hydrogen atmosphere of 10 atm.

The reaction mixture was filtered through a celite pad and the resulting filtrate was concentrated under reduced pressure to obtain 64.48 g (100%) of the title compound.

$^1$H-NMR (400 MHz, CDCl$_3$) δ: 1.53–1.59(1H,m), 1.72–1.76(1H,m), 1.92(3H,s), 2.46(1H,dd,J=8.4 Hz,12.6 Hz), 2.77–2.87(3H,m), 2.96(1H,dd,J=5.6 Hz,13.5 Hz), 2.91–3.48(1H,m), 4.21–4.23(1H,m), 5.89(1H,d,J=7.0 Hz), 7.13–7.29 (1OH,m).

EI-MS (m/z)326.

REFERENCE EXAMPLE 3

Synthesis of (2S, 3S, 5S)-2,5-diamino-1,6-diphenyl-3-hexanol Dihydrochloride To 325 ml of 3N hydrochloric acid, was added 64.84 g of (2S, 3S, 5S)-2-amino-5-acetylamino-1,6-diphenyl-3-hexanol, and the resulting solution was refluxed for 6 hours, chilled with ice water and then neutralized with 3N sodium hydroxide to separate an oil, which was extracted with n-butanol. The organic layer was concentrated to dryness under reduced pressure, thereby obtaining 66.62 g of a viscous oil. This oil was dissolved in 600 ml of isopropanol. To the solution, 100 ml of concentrated hydrochloric acid was added to reflux the mixture for 1 hour. The reaction mixture was chilled and allowed to stand in a refrigerator. The precipitate formed was then filtered to obtain 50.28 g of the title compound (71.1%, purity: 99.1%) as colorless powder. The mother liquor was concentrated, and the residue was chilled to form precipitate, thereby obtaining 28 g (11.81%) of the second crop.

m.p.>248° C. (decomposed)

$^1$H-NMR (400 MHz, D$_2$O) δ: 1.85–1.95(2H,m), 2.85–2.98(2H,m), 3.04–3.10(2H,m), 3.49–3.51(1H,m), 3.73–3.77(1H,m), 3.84–3.86(1H,m), 7.28–7.44(10H,m).

[α]$_D^{20}$ −28.24° (C=1.03, H$_2$O).

REFERENCE EXAMPLE 4

Synthesis of (2S,3S,5S)-2-(N,N-dibenzylamino)-5-amino-1,6-diphenyl-3-hexanol To 40 ml of 4N hydrochloric acid, was added 10.86 g of (2S,3S,5S)-2-(N,N-dibenzylamino)-5-acetylamino-1,6-diphenyl-3-hexanol, and the resulting solution was refluxed for 6 hours and cooled to room temperature. To the reaction mixture, was added 30 ml of n-butanol, and the resulting mixture was neutralized with dropwise addition of a 10% solution of sodium hydroxide. The organic layer of n-butanol was separated, washed with water, dried over sodium sulfate and concentrated to dryness under reduced pressure, thereby obtaining 9.29 g (100%) of the title compound as a colorless resin. This compound was found to be a single compound by high performance liquid chromatography (HPLC), and hence used in the subsequent process without further purification.

REFERENCE EXAMPLE 5

Synthesis of (2S)-2-(N,N-dibenzylamino)-5-acetylamino-1,6-diphenyl-4-hexen-3-one (2S)-2-(N,N-dibenzylamino)-5-amino-1,6-diphenyl-4-hexene-3-one (100.0 g, 214.1 mmol) was dissolved in toluene (500 ml), to which pyridine (10 ml, 124.3 mmol) was added under a nitrogen stream. Acetyl chloride (25.7 g, 321.1 mmol) was slowly added to the resultant mixture while chilling with ice water so as not to raise the temperature above 10° C. The reaction mixture was further stirred at 50° C. for 5 hours and 25° C. for 16 hours. The mixture was then washed twice with a small amount of a 10% aqueous solution of sodium carbonate and with an aqueous sodium chloride, and dried over sodium sulfate. The solvent was distilled off under reduced pressure, and the resulting crude product was recrystallized from methanol (1000 ml), thereby obtaining the title compound (97.5 g, 89.4%) as pale yellow crystals.

m.p. 95°–96° C.

[α]$_D^{24}$ −210.0° (C=1.17, CHCl$_3$)

IR (KBr, cm$^{-1}$) v: 1705, 1650.

$^1$H-NMR (400 MHz, CDCl$_3$) δ: 2.15(3H,s), 2.91(1H,dd, J=4.3 Hz,13.7 Hz), 3.15 (1H, dd,J=8.8 Hz, 13.7 Hz), 3.44 (1H,dd,J=4.3 Hz,8.8 Hz), 3.57(2H,d,J=13.7 Hz), 3.65(2H, d,J=13.7 Hz), 4.08(1H,d,J=17.1 Hz), 4.32(1H,d,J=17.1 Hz), 7.02–7.50(20H,m), 12.25 (1H,s).

Example 1 to Example 14 relate to the synthesis of (2S, 5S)-2-(N,N-dibenzylamino)-5-acetylamino-1,6-diphenyl-3-hexanone.

EXAMPLE 1

An autoclave was charged with (2S) -2-(N,N-dibenzylamino)-5-acetylamino-1,6-diphenyl-4-hexen-3-one (10.0 g, 20 mmol) synthesized in Reference Example 5, 0.5 g of 3%-Pd-alumina and 40 ml of acetone. The contents were chilled to 5° C. and stirred under a hydrogen pressure of 5 atm at 4°–14° C. for 29.5 hours. The reaction mixture was filtered through a celite pad to remove the catalyst. The filtrate was concentrated under reduced pressure to obtain 9.55 g (yield: 96%) of the title compound. HPLC indicated that (2S,5S)/(2S,5R) was 93.4/6.6. The crude product was recrystallized from a mixed solvent of 20 ml of ethyl acetate and 60 ml of heptane to obtain 6.96 g (yield: 69.3%) of the title compound. HPLC indicated that (2S,5S)/(2S,5R) was 99.0/1.0.

m.p. 90°–91° C.

[α]$_D^{24}$ −83.4° (C=1.086, CHCl$_3$)

IR (KBr, cm$^{-1}$) v: 3350, 1720, 1650.

$^1$H-NMR (400 MHz, CDCl$_3$) δ: 1.63 (3H,s), 2.38(1H,dd, J=5.0&17.3 Hz), 2.77(2H,d,J=6.0 Hz), 2.79(1H,d,J= 6.0&17.3 Hz), 2.91(1H,dd,J=4.1&13.3 Hz), 3.12(1H,dd,J= 9.4&13.3 Hz), 3.53(1H,dd,J=4.1&9.4 Hz), 3.57(2H,d,J= 13.8 Hz), 3.78(2H,d,J=13.8 Hz), 4.2–4.4(1H,m), 5.45(1H, d,J=8.9 Hz), 7.0–7.4(20H,m).

EXAMPLE 2

An autoclave was charged with (2S)-2-(N,N-dibenzylamino)-5-acetylamino-1,6-diphenyl-4-hexen-3-one (0.5 g, 1 mmol) synthesized in Reference Example 5, 15 mg of 3%-Pd-alumina and 5 ml of acetone. The contents were stirred under a hydrogen pressure of 50 atm at 50° C. for 14.5 hours. The reaction mixture was filtered through a celite pad to remove the catalyst. The filtrate was concentrated under reduced pressure to obtain 0.48 g (yield: 96%) of the same compound as that obtained in Example 1. HPLC of the reaction mixture indicated that (2S,5S)/(2S,5R) was 90.0/10.0.

EXAMPLE 3

According to the procedure similar to that described in Example 2, (2S)-2-(N,N-dibenzylamino)-5-acetylamino-1,6-diphenyl-4-hexen-3-one (0.5 g, 1 mmol) synthesized in Reference Example 5 was hydrogenated in different solvents (5 ml) under conditions of varied catalysts, amounts of the catalysts, hydrogen pressures, reaction temperatures and reaction time. The results are shown in Table 1.

mmol) synthesized in Reference Example 5, 50 mg of 5%-Rh-alumina and 20 ml of ethyl acetate. The contents were stirred under a hydrogen pressure of 50 atm at room temperature for 2 days. The reaction mixture was filtered through a celite pad to remove the catalyst. The filtrate was concentrated under reduced pressure to obtain 1.25 g (yield: 83%) of the same compound as that obtained in Example 2. HPLC indicated that (2S,5S)/(2S,5R) was 74.4/25.6.

EXAMPLE 5

According to the procedure similar to that described in Example 2, (2S)-2-(N,N-dibenzylamino)-5-acetylamino-1,6-diphenyl-4-hexen-3-one (0.5 g, 1 mmol) synthesized in Reference Example 5 was reduced using 5 mg of 5%-Rh-$Al_2O_3$ (alumina) as a catalyst under conditions of varied solvents, amounts of the solvents, hydrogen pressures, reaction temperatures and reaction time. The results are shown in Table 2.

TABLE 1

| No. | Catalyst | [mg] | Solvent | Hydrogen pressure (atm) | Temperature (°C.) | Time (hr) | Yield (%) | (2S,5S)/(2S,5R) |
|---|---|---|---|---|---|---|---|---|
| 1 | 5%-Pd-alumina | 15 | Acetone | 50 | 50 | 1.5 | 97 | 87.2/12.2 |
| 2 | 5%-Pd-alumina | 15 | Acetone | 30 | 50 | 17 | 97 | 91.9/8.1 |
| 3 | 5%-Pd-alumina | 25 | 2-Butanone | 5 | Room temp. | 23.5 | 98 | 92.9/7.10 |
| 4 | 5%-Pd-silica-alumina | 15 | Acetone | 50 | Room temp. | 4 | 94 | 91.6/8.4 |
| 5 | 5%-Pd-silica-alumina | 15 | Acetone | 10 | Room temp. | 19 | 97 | 93.5/6.5 |
| 6 | 5%-Pd-silica-alumina | 15 | 2-Butanone | 30 | 50 | 13 | 70 | 90.0/10.0 |
| 7 | 5%-Pd-alumina | 15 | Acetone | 10 | 50 | 4 | 96 | 91.6/8.4 |
| 8 | 5%-Pd-alumina | 15 | Acetone | 5 | 5 | 18 | 86 | 94.2/5.8 |
| 9 | 5%-Pd-alumina | 15 | Methanol | 50 | 50 | 2 | 67 | 78.1/21.9 |
| 10 | 5%-Pd-alumina | 15 | Acetone | 50 | 50 | 8.5 | 43 | 87.6/12.4 |
| 11 | 3%-Pd-alumina | 25 | Acetone | 2 | Room temp. | 22 | 97 | 93.5/6.5 |
| 12 | 3%-Pd-alumina | 25 | Acetone | 2 | 5 | 18 | 80 | 94.1/5.9 |
| 13 | 3%-Pd-alumina | 25 | Ethyl acetate | 10 | 50 | 6 | 67 | 88.9/11.1 |
| 14 | 3%-Pd-alumina | 25 | Tetrahydrofuran | 30 | 50 | 5 | 95 | 90.8/9.2 |
| 15 | 3%-Pd-alumina | 25 | Toluene | 30 | 50 | 18 | 93 | 86.8/13.2 |
| 16 | 3%-Pd-alumina | 25 | Isopropanol | 10 | 50 | 5 | 98 | 89.0/11.0 |
| 17 | 3%-Pd-alumina | 25 | 1,2-Dimethoxyethane | 10 | 50 | 23.5 | 74 | 87.6/12.4 |
| 18 | 3%-Pd-alumina | 25 | Methyl isobutyl ketone | 10 | 50 | 7 | 96 | 89.4/10.6 |
| 19 | 3%-Pd-alumina | 25 | Diisopropyl ketone | 10 | Room temp. | 7 | 76 | 89.8/10.2 |
| 20 | 3%-Pd-alumina | 25 | Dioxane | 30 | 50 | 22 | 39 | 86.9/13.1 |

EXAMPLE 4

An autoclave was charged with (2S)-2-(N,N-dibenzylamino)-5-acetylamino-1,6-diphenyl-4-hexen-3-one (1.5 g, 3

TABLE 2

| No. | Solvent | Hydrogen pressure (atm) | Temperature (°C.) | Time (hr) | Yield (%) | (2S,5S)/(2S,5R) |
|---|---|---|---|---|---|---|
| 1 | Ethyl acetate(7 ml) + triethylamine(0.14 ml) | 50 | Room temp. | 20 | 77 | 79.2/20.7 |
| 2 | Ethyl acetate(7 ml) + borotrifluoride etherate(0.13 ml) | 50 | Room temp. | 71 | 65 | 74.4/25.6 |
| 3 | Ethyl acetate(7 ml) + water(0.018 ml) | 50 | Room temp. | 28.5 | 69 | 74.8/25.2 |
| 4 | Ethyl acetate(7 ml) + triethylene(0.14 ml) | 50 | 50 | 3.5 | 88 | 76.4/23.6 |
| 5 | Acetone(5ml) + diisopropylethylamine(0.11 ml) | 50 | 50 | 5 | 88 | 77.9/22.1 |
| 6 | Methyl isobutyl ketone(5 ml) + triethylene(0.14 ml) | 50 | 50 | 6 | 88 | 78.6/21.4 |
| 7 | Methyl isobutyl ketone(5 ml) + diisopropylethylamine (0.11 ml) | 50 | 50 | 3.5 | 81 | 77.5/22.5 |
| 8 | Diisopropyl ketone(5 ml) + triethylamine(0.14 ml) | 50 | 50 | 6.5 | 85 | 78.6/21.4 |

TABLE 2-continued

| No. | Solvent | Hydrogen pressure (atm) | Temperature (°C.) | Time (hr) | Yield (%) | (2S,5S)/(2S,5R) |
|---|---|---|---|---|---|---|
| 9 | 2-Butanone(5 ml) + triethylamine(0.14 ml) | 50 | 50 | 6 | 87 | 78.1/21.9 |
| 10 | Triethylamine(5 ml) | 50 | 50 | 10 | 56 | 79.0/21.0 |
| 11 | Acetylacetone(5 ml) + triethylamine(0.14 ml) | 50 | 50 | 8 | 66 | 83.5/16.5 |

EXAMPLE 6

A 50-ml flask equipped with a three-way cock was charged with 8.4 mg (0.01 mmol) of [Rh(cod)$_2$]ClO$_4$ and 8.0 mg (0.01 mmol) of 1,2-bis(diphenylphosphino)ethane. After purging the flask with nitrogen, 5 ml of methanol was added to the contents, and the resulting mixture was stirred for 1 hour to prepare a catalyst solution. On the other hand, 0.5 g (1 mmol) of (2S)-2-(N,N-dibenzyl-amino)-5-acetylamino-1,6-diphenyl-4-hexen-3-one synthesized in Reference Example 5 was weighed out in a 100-ml stainless steel autoclave. After purging the autoclave with nitrogen, the catalyst solution prepared above was added by a syringe to the autoclave. Thereafter, a reaction was conducted under a hydrogen pressure of 100 atm at 20° C. for 20 hours. HPLC of the reaction mixture indicated that conversion to the same compound as that obtained in Example 1 was 23.3%, and (2S,5S)/(2S,5R) was 68/32.

EXAMPLE 7

According to the procedure similar to that described in Example 6, 0.5 g of (2S)-2-(N,N-dibenzylamino)-5-acetylamino-1,6-diphenyl-4-hexen-3-one was hydrogenated in 5 ml of methanol using [Rh(cod)$_2$]ClO$_4$ under conditions of varied ligands, molar ratios of substrate to catalyst (S/C), hydrogen pressures and reaction temperatures. The results are shown in Table 3.

pressure of 50 atm at 20° C. for 20 hours. HPLC of the reaction mixture indicated that conversion to the same compound as that obtained in Example 1 was 39.2%, and (2S,5S)/(2S,5R) was 70/30. Here, PPh$_3$ means triphenylphosphine.

EXAMPLE 9

According to the procedure similar to that described in Example 8, 0.5 g of (2S)-2-(N,N-dibenzylamino)-5-acetylamino-1,6-diphenyl-4-hexen-3-one was hydrogenated in 5 ml of methanol using varied organometallic complex catalysts. The results are shown in Table 4.

TABLE 3

| No. | Ligand | Hydrogen pressure (atm) | Temperature (°C.) | Time (hr) | Yield (%) | (2S,5S)/(2S,5R) |
|---|---|---|---|---|---|---|
| 1 | 1,4-Bis(diphenylphosphino)butane | 50 | 20 | 20 | 59.2 | 72/28 |
| 2 | 1,4-Bis(diphenylphosphino)butane | 50 | 50 | 20 | 65.2 | 76/24 |
| 3 | Triphenylphosphine | 50 | 20 | 20 | 14.3 | 90/10 |
| 4 | (2S,3S)-Bis(diphenylphosphino)butane | 100 | 50 | 20 | 94.3 | 87/13 |
| 5 | (2R,3R)-Bis(diphenylphosphino)butane | 50 | 20 | 20 | 17.9 | 36/64 |
| 6 | (R)-TolBINAP | 50 | 20 | 20 | 59.2 | 72/28 |
| 7 | (S)-TolBINAP | 50 | 20 | 20 | 33.7 | 67/35 |

TolBINAP denotes 2,2-bis[di(p-tolyl)phosphino]-1,1-binaphthyl.

EXAMPLE 8

A 50-ml flask equipped with a three-way cock was charged with 19.2 mg (0.02 mmol) of RuCl$_2$(PPh$_3$)$_3$ and 0.5 g (1 mmol) of (2S)-2-(N,N-dibenzyl-amino)-5-acetylamino-1,6-diphenyl-4-hexen-3-one synthesized in Reference Example 5. After purging the flask with nitrogen, 5 ml of methanol was added to the contents, and the resulting mixture was stirred for 1 hour to prepare a solution containing the catalyst. The solution was poured by a syringe into a 100-ml stainless steel autoclave purged with nitrogen. Thereafter, a reaction was conducted under a hydrogen

TABLE 4

| No. | Ligand | S/C | Hydrogen pressure (atm) | Temperature (°C.) | Yield (%) | (2S,5S)/(2S,5R) |
|---|---|---|---|---|---|---|
| 1 | Ru$_2$Cl$_4$(1,4-DIPHOS)$_2$(NEt$_3$) | 50 | 50 | 20 | 14.6 | 86/141 |
| 2 | Ru(OAc)$_2$[(S)-TolBINAP] | 50 | 50 | 20 | 26.1 | 81/19 |
| 3 | Ru(OAc)$_2$[(R)-BINAP] | 50 | 50 | 20 | 20.1 | 67/33 |
| 4 | [RuI(p-cymene)((S)-TolBINAP)]I | 50 | 50 | 20 | 22.1 | 67/33 |
| 5 | [RuI(p-cymene)((R)-TolBINAP)]I | 50 | 50 | 20 | 19.6 | 72/28 |

Ac denotes an acetyl group.
1,4-DIPHOS denotes 1,4-bis(diphenylphosphino)butane.
NEt$_3$ denotes triethylamine.

EXAMPLE 10

A 100-ml stainless steel autoclave purged with nitrogen was charged with 16.5 mg (0.0267 mmol) of [Cp*RhCl$_2$]$_2$, 0.1 ml of triethylamine and 10 ml of isopropyl alcohol. The contents were stirred under a hydrogen pressure of 50 atm at room temperature for 20 hours. To the mixture, was added 0.5 g (1 mmol) of (2S)-2-(N,N-dibenzyl-amino)-5-acetylamino-1,6-diphenyl-4-hexen-3-one synthesized in Reference Example 5 and stirred under a hydrogen pressure of 50 atm at room temperature for 18 hours. HPLC of the reaction mixture indicated that the same compound as that obtained in Example 1 was obtained with conversion of 54%, selectivity of 52% and (2S,5S)/(2S,5R) of 83.4/16.6. Here, Cp* means pentamethylcyclopentadiene.

EXAMPLE 11

According to the procedure similar to that described in Example 10, 0.5 g (1 mmol) of (2S)-2-(N,N-dibenzyl-amino)-5-acetylamino-1,6-diphenyl-4-hexen-3-one was hydrogenated in 10 ml of isopropanol under conditions of varied organometallic complex catalysts, amounts of triethylamine, reaction temperatures and reaction time. The results are shown in Table 5.

dryness under reduced pressure, thereby activating the catalyst. Under a nitrogen stream, a 100-ml autoclave was charged with the catalyst activated in the above-described manner, 0.5 g (1 mmol) of the compound synthesized in Reference Example 5 and 10 ml of isopropyl alcohol. A reaction was conducted under a hydrogen pressure of 50 atm at room temperature for 17 hours. HPLC of the reaction mixture indicated that the same compound as that obtained in Example 1 was obtained with conversion of 3.6% and (2S,5S)/(2S,5R) of 87.4/12.6.

EXAMPLE 13

Under a nitrogen stream, a 100-ml autoclave was charged with 0.5 g (1 mmol) of the compound synthesized in Reference Example 5, 3.9 mg (0.00495 mmol) of [IrCp*Cl$_2$]$_2$, 0.02 ml of triethylamine and 5 ml of isopropyl alcohol. A reaction was conducted under a hydrogen pressure of 50 atm at 70° C. for 20 hours. HPLC of the reaction mixture indicated that the same compound as that obtained in Example 1 was obtained with conversion of 28.8%, selectivity of 80% and (2S,5S)/(2S,5R) of 91.9/8.1.

EXAMPLE 14

According to the procedure similar to that described in Example 13, 0.5 g of (2S)-2-(N,N-dibenzyl-amino)-5-

TABLE 5

| No. | Catalyst | [mg] | Et$_3$N (m) | Hydrogen pressure (atm) | Temperature (°C.) | Time (hr) | Yield (%) | (2S,5S)/(2S,5R) |
|---|---|---|---|---|---|---|---|---|
| 1 | [RhCl$_2$Cp*]$_2$ | 1.3 | 0.01 | 50 | 50 | 48 | 24.8 | 79.6/20.4 |
| 2 | [IrCl$_2$Cp*]$_2$ | 19.3 | 0.1 | 50 | Room temp. | 66 | 33.9 | 93.7/6.3 |
| 3 | [IrCl$_2$Cp*]$_2$ | 7.8 | 0.04 | 50 | 50 | 14 | 5.3 | 97.4/2.6 |

EXAMPLE 12

To 33 mg (0.0495 mmol) of [(C$_6$Me$_6$)RuCl$_2$]$_2$, were added 10 ml of isopropyl alcohol and 10 ml of a 1M aqueous solution of sodium carbonate. After the mixture was stirred at 80° C. for 30 minutes, the solvent was distilled off under reduced pressure. The resultant residue was extracted with chloroform, and the chloroform layer was concentrated to acetylamino-1,6-diphenyl-4-hexen-3-one was hydrogenated in 10 ml of different solvents under conditions of varied organometallic complex catalysts, amounts of triethylamine, amounts of solvent, hydrogen pressures, reaction temperatures and reaction time. The results are shown in Table 6.

TABLE 6

| No. | Catalyst | [mg] | Solvent | Et$_3$N (ml) | Hydrogen pressure (atm) | Temperature (°C.) | Time (hr) | Yield (%) | (2S,5S)/(2S,5R) |
|---|---|---|---|---|---|---|---|---|---|
| 1 | [RhCl$_2$Cp*]$_2$ | 15.4 | Isopropanol | 0.1 | 50 | 50 | 13 | 40.0 | 83.5/16.5 |
| 2 | [IrCl$_2$Cp*]$_2$ | 3.9 | Isopropanol | 0.02 | 50 | 50 | 42 | 23.6 | 93.5/6.5 |

TABLE 6-continued

| No. | Catalyst | [mg] | Solvent | Et₃N (ml) | Hydrogen pressure (atm) | Temperature (°C.) | Time (hr) | Yield (%) | (2S,5S)/(2S,5R) |
|---|---|---|---|---|---|---|---|---|---|
| 3 | [IrCl₂Cp*]₂ | 3.9 | Isopropanol | 0.02 | 50 | Room temp. | 42 | 1.7 | 92.1/7.9 |
| 4 | [IrCl₂Cp*]₂ | 4.1 | Tetrahydrofuran | 0.02 | 50 | 50 | 15 | 4.5 | 89.7/10.3 |
| 5 | [IrCl₂Cp*]₂ | 4.3 | Isopropanol | 0.02 | 30 | 50 | 17 | 2.9 | 97.2/2.8 |
| 6 | [IrCl₂Cp*]₂ | 3.8 | Isopropanol | 0.02 | 50 | 50 | 17 | 4.2 | 98.2/1.9 |
| 7 | [IrCl₂Cp*]₂ | 3.8 | Isopropanol | 0.02 | 80 | 50 | 17 | 6.6 | 96.5/3.5 |
| 8 | [IrCl₂Cp*]₂ | 3.9 | Isopropanol | 0.02 | 50 | 50 | 42 | 1.3 | 93.5/6.5 |
| 9 | [IrCl₂Cp*]₂ | 4.0 | Phenethyl alcohol | 0.02 | 50 | 50 | 18 | 2.3 | 88.2/11.9 |
| 10 | [Rh(cod)Cp*] | 2.8 | Isopropanol | 0 | 50 | Room temp. | 17 | 7.7 | 77.8/22.2 |
| 11 | [Rh(cod)Cp*] | 2.8 | Isopropanol | 0 | 50 | 50 | 17 | 31.4 | 79.7/20.3 |
| 12 | [Rh(cod)Cp*] | 2.9 | Isopropanol | 0.02 | 50 | 50 | 17 | 51.8 | 78.2/21.8 |
| 13 | [Rh(cod)C₆Me₆]BF₄ | 4.5 | Isopropanol | 0 | 50 | 50 | 19 | 8.0 | 76.9/23.1 |
| 14 | [Rh(cod)C₆Me₆]BF₄ | 5.1 | Isopropanol | 0.02 | 50 | 50 | 19 | 49.9 | 76.2/23.7 |
| 15 | [IrI₂Cp*]₂ | 5.9 | Isopropanol | 0.02 | 50 | 50 | 18 | 24.3 | 92.7/7.3 |

EXAMPLE 15

Synthesis of (2S,5S)-2-(N,N-dibenzylamino)-5-tert-butoxy-carbonylamino-1,6-diphenyl-3-hexanone An autoclave was charged with (2S)-2-(N,N-dibenzylamino)-5-tert-butoxycarbonylamino-1,6-diphenyl-4-hexen-3-one (0.56 g, 1 mmol), 25 mg of 3%-Pd-alumina and 5 ml of acetone. After introducing hydrogen under a pressure of 10 atm, the contents were stirred at 50° C. for 9 hours. The reaction mixture was filtered through a celite pad to remove the catalyst, and the filtrate was concentrated under reduced pressure to obtain 0.47 g (yield: 83%) of the title compound. ¹H-NMR indicated that the purity of the (2S,5S) isomer was 95% or higher.

IR (neat, cm⁻¹) ν: 3415, 1715.

¹H-NMR (400 MHz, CDCl₃) δ: 1.32(9H,s), 2.36–2.41 (1H,m), 2.72 (1H,dd,J=6.7&16.7 Hz), 2.93(1H,dd,J=5.0&13.4 Hz), 3.06(1H,dd,J=8.4&13.2 Hz), 3.57(2H,d,J=13.3 Hz), 3.72(2H,d,J=13.5 Hz), 3.99–4.03(1H,m), 7.01–7.29(20H,m).

REFERENCE EXAMPLE 6

Synthesis of (2S,5S)-2-(N,N-dibenzylamino)-5-pivaloyl-amino-1,6-diphenyl-4-hexen-3-one (2S)-2-(N,N-dibenzylamino)-5-amino-1,6-diphenyl-4-hexene-3-one (5.8 g, 9 mmol) was dissolved in 100 ml of toluene. To the resulting solution, 5 ml of pyridine and 5 ml of pivaloyl chloride were gradually added while chilling with ice water. The reaction mixture was stirred at 70° C. for 5 hours to conduct reaction, followed by chilling with ice water. To the reaction mixture, was added 5 ml of water, and the mixture was left to stand for 1 hour. The reaction mixture was then washed with 50 ml of water and 50 ml of a dilute solution of potassium hydrogensulfate, and further with water, dried over sodium sulfate, and concentrated under reduced pressure. The residue was purified by silica gel column chromatography using n-hexane-ethyl acetate (10:1) as an eluent, thereby obtaining 4.49 g (76.9%) of the title compound as colorless needle crystals.

m.p. 118.0°–118.2° C.

IR (KBr, cm⁻¹) ν: 3030, 2980, 1705, 1640, 1590, 1460, 1210, 750, 700.

¹H-NMR (CDCl₃, δppm): 1.28(9H,s), 2.89(1H,dd,J=5&14 Hz), 3.15(1H,dd,J=9&14 Hz), 3.41(1H,dd,J=5&9 Hz), 3.59(4H,ABq), 4.22(2H,ABq), 5.40(1H,d,J<1 Hz), 7.0–7.5(20H,m), 12.52(1H,br,s).

EXAMPLE 16

Synthesis of (2S,5S)-2-(N,N-dibenzylamino)-5-pivaloyl-amino-1,6-diphenyl-3-hexanone To a solution of 0.5 g of (2S)-2-(N,N-dibenzyl-amino)-5-pivaloylamino-1,6-diphenyl-4-hexen-3-one in acetone (5 ml), was added 25 mg of 3%-Pd-alumina, and the reaction mixture was stirred under a hydrogen pressure of 10 atm at 50° C. for 24 hours. HPLC of the reaction mixture indicated that the conversion of the title compound was 97%, and (2S,5S)/(2S,5R) was 94.2/5.8. The reaction mixture was filtered, and the filtrate was concentrated under reduced pressure. The resulting residue was recrystallized from n-hexane to obtain 352 mg (70.1%) of the title compound as colorless needle crystals.

(2S,5S)/(2S,5R)=98.2/1.8 m.p. 122°–123° C.

IR (KBr, cm⁻¹) ν: 3450, 1705, 1670, 1510, 1500, 750, 700.

¹H-NMR (CDCl₃, δppm): 0.94(9H,s), 2.34(1H,dd,J=5&18 Hz), 2.7–3.0(4H,m), 3.11(1H,dd,J=9&13 Hz), 3.54 (1H,dd,J=4&9 Hz), 3.68(4H,ABq), 4.27(1H,m), 6.01(1H,d, J=9 Hz), 7.0–7.5(20H,m).

REFERENCE EXAMPLE 7

Synthesis of (2S)-2-(N,N-dibenzylamino)-5-ethoxycarbonyl-amino-1,6-diphenyl-4-hexen-3-one A solution of 5 g of (2S)-2-(N,N-dibenzylamino)-5-amino-1,6-diphenyl-4-hexene-3-one in toluene (100 ml) was chilled with ice water. To the solution, 5 ml of pyridine and 5 ml of ethyl chloroformate were gradually added. The reaction mixture was stirred at 70° C. for 12 hours, and then chilled with ice water. 5 ml of water was added to the reaction mixture, and the mixture was held at the same temperature for 1 hour. The reaction mixture was then washed with 50 ml of water and 50 ml of a dilute solution of potassium hydrogensulfate, and further with water, dried over sodium sulfate, and concentrated under reduced pressure. The residue was purified by silica gel column chromatography using n-hexane-ethyl acetate (10:1) as an eluent, thereby obtaining 1.65 g (28.5%) of the title compound as pale yellow powder from the eluate.

m.p. 91°–93° C.

IR (KBr, cm⁻¹) ν: 3030, 1745, 1650, 1595, 1495, 1195, 705.

¹H-NMR (CDCl₃, δppm): 1.28(3H,5,J=7 Hz), 2.89(1H, dd,J=4&14 Hz), 3.13(1H,dd,J=9&14 Hz), 3.42(1H,dd,J=

4&9 Hz), 3.60(4H,ABq), 4.14(2H,ABq), 5.34(1H,t,J<1 Hz), 7.0–7.5(20H,m), 11.87(1H,br,s).

EXAMPLE 17

Synthesis of (2S,5S)-2-(N,N-dibenzylamino)-5-ethoxy-carbonylamino-1,6-diphenyl-3-hexanone To a solution of 0.5 g of (2S)-2-(N,N-dibenzylamino)-5-ethoxycarbonylamino-1,6-diphenyl-4-hexen-3-one in 5 ml of acetone, was added 25 mg of 3%-Pd-alumina, and the reaction mixture was stirred under a hydrogen pressure of 10 atm at 50° C. for 24 hours. HPLC of the reaction mixture indicated that conversion to the title compound was 99% or higher, and (2S,5S)/(2S,5R) was 92.0/8.0. The reaction mixture was filtered, and the filtrate was concentrated under reduced pressure to obtain a theoretical amount of the title compound as a viscous oil.

IR (KBr, cm$^{-1}$) v: 3450, 3030, 1720, 1695, 1535, 1215, 750, 700.

$^1$H-NMR (CDCl$_3$, δppm): 1.14(3H,t,J=7 Hz), 2.32(1H, dd,J=6&18 Hz), 2.65–2.85(3H,m), 2.91(1H,dd,J=4&13 Hz), 3.13(1H,dd,J=9&13 Hz), 3.52(1H,dd,J=4&9 Hz), 3.67(4H, ABq), 3.99(2H,q,J=7 Hz), Ca. 4.0(1H,m), 7.0–7.5(20H,m).

REFERENCE EXAMPLE 8

Synthesis of (2S)-2-(N,N-dibenzylamino)-5-trifluoro-acetylamino-1,6-diphenyl-4-hexen-3-one A reaction was conducted in the same manner as in Reference Example 7 except that 5 ml of trifluoroacetic anhydride was used instead of 5 ml of ethyl chloroformate, thereby obtaining 3.30 g (83.6%) of the title compound as a yellow oil.

IR (KBr, cm$^{-1}$) v: 3030, 1745, 1660, 1620, 1605, 1500, 1230, 700.

$^1$H-NMR (CDCl$_3$, δppm): 2.91(1H,dd,J=4&14 Hz), 3.17 (1H,dd,J=9&14 Hz), 3.42(1H,dd,J=4&14 Hz), 3.59(4H, ABq), 4.17(2H,ABq), 5.63(1H,t,J<1 Hz), 7.0–7.5(20H,m).

EXAMPLE 18

Synthesis of (2S,5S)-2-(N,N-dibenzylamino)-5-trifluoro-acetylamino-1,6-diphenyl-3-hexanone A reaction was conducted in the same manner as in Example 17 except that a solution in 5 ml of acetone of 0.5 g of (2S)-2-(N,N-dibenzyl-amino)-5-trifluoroacetyl-amino-1,6-diphenyl-4-hexen-3-one obtained in Reference Example 8 was used. HPLC of the reaction mixture indicated that conversion to the title compound was 99% or higher, and (2S,5S)/(2S,5R) was 90.1/9.9. The reaction mixture was filtered, and the filtrate was concentrated to obtain the title compound in a glassy form in a theoretical yield.

IR (KBr, cm$^{-1}$) v: 3450, 3030, 1720, 1705, 1500, 1180, 750, 700.

$^1$H-NMR (CDCl$_3$, δppm): 0.8–0.9(1H,m), 1.2–1.3(1H, m), 2.22(1H,dd,J=5 Hz,18 Hz), 2.85(2H,d,J=7 Hz), 2.9–3.0 (2H,m), 3.14(1H,dd,J=10 Hz,13 Hz), 3.50(1H,dd,J=4 Hz,10 Hz), 3.70(4H,ABq), 4.28(1H,m), 7.0–7.5(20H,m).

REFERENCE EXAMPLE 9

Synthesis of (2S)-2-(N,N-dibenzylamino)-5-benzoylamino-1,6-diphenyl-4-hexen-3-one A reaction was conducted in the same manner as in Reference Example 7 except that 5 ml of benzoyl chloride was used instead of 5 ml of ethyl chloroformate. The resultant reaction mixture was purified by silica gel column chromatography using n-hexane-ethyl acetate (7:1) as an eluent, thereby obtaining 3.3 g (54.4%) of the title compound from the eluate.

The compound was recrystallized from ethyl acetate-n-hexane to obtain 2.74 g (45.2%) of yellow plate crystals.

m.p. 131°–133° C.

IR (KBr, cm$^{-1}$) v: 3030, 1695, 1640, 1605, 1590, 1480, 1250, 700.

$^1$H-NMR (CDCl$_3$, δppm): 2.93(1H,dd,J=5&14 Hz), 3.38 (1H,dd,J=9&14 Hz), 3.47(1H,dd,J=5&9 Hz), 3.62(4H, ABq), 4.38(2H,ABq), 5.49(1H,t,J<1 Hz), 7.0–7.5(23H,m), 8.02(2H,d,J=7 Hz), 13.27 (1H,br,s).

EXAMPLE 19

Synthesis of (2S,5S)-2-(N,N-dibenzylamino)-5-benzoylamino-1,6-diphenyl-3-hexanone A reaction was conducted in the same manner as in Example 17 except that (2S)-2-(N,N-dibenzylamino)-5-benzoylamino-1,6-diphenyl-4-hexen-3-one obtained in Reference Example 9 was used. HPLC of the reaction mixture indicated that conversion to the title compound was 99% or higher, and (2S,5S)/(2S,5R) was 89.9/10.1. The reaction mixture was filtered, and the filtrate was concentrated under reduced pressure to obtain a theoretical amount of the title compound as a viscous oil.

IR (KBr, cm$^{-1}$) v: 3030, 1710, 1650, 1510, 1495, 1295, 750, 700.

$^1$H-NMR (CDCl$_3$, δppm): 2.43 (1H,dd,J=5&18 Hz), 2.9–3.0(4H,m), 3.13(1H,dd,J=5&14 Hz), 3.5–3.6(1H,m), 3.69(4H,ABq), 4.4–4.6(1H,m), 7.1–7.6(25H,m).

What is claimed is:

1. A process for producing a (2S,5S)-2,5-diamino-1,6-diphenyl-3-hexanone derivative represented by the formula (1):

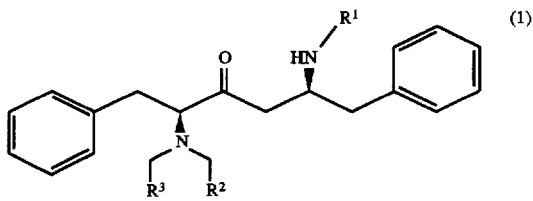

wherein R$^1$ means a lower alkylcarbonyl group, a halogen-substituted lower alkylcarbonyl group, an arylcarbonyl group or a lower alkoxycarbonyl group, and R$^2$ and R$^3$ are identical with or different from each other and denote individually an aryl group or an alkoxy-substituted aryl group, which comprises subjecting a (2S)-2,5-diamino-1,6-diphenyl-4-hexen-3-one derivative represented by the formula (2):

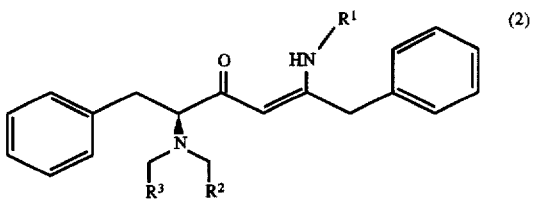

wherein R$^1$, R$^2$ and R$^3$ have the same meaning as defined above, to a hydrogenation reaction in the presence of a transition metal-containing catalyst, wherein said transition metal-containing catalyst is either a mononuclear complex represented by the formula (3):

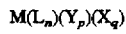
(3)

wherein M is ruthenium, rhodium, palladium or iridium, L denotes an organophosphorus compound represented by the formula (6):

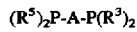
(6)

wherein $R^5$ means a lower alkyl group, a phenyl group or a tolyl group, and A denotes the formula (7):

(7)

in which $R^6$ and $R^7$ mean individually a lower alkyl group, or $R^6$ and $R^7$ are bonded to each other to form a ring, and m stands for a number of 0–8, or the formula (8):

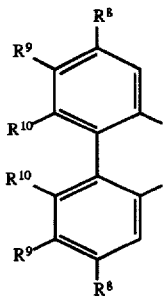
(8)

wherein $R^{10}$ means a methyl group, and $R^8$ and $R^9$ denote individually a hydrogen atom, a halogen atom or a lower alkyl group, with the proviso that $R^9$ and $R^{10}$ may form together a carbocyclic or aryl ring, Y stands for cyclooctadiene, norbornadiene, p-cymene, acetonitrile, ethylene, pyridine, acetic acid or benzene, X is a halogen ion, sulfonate ion, acetate ion, nitrile ion, $ClO_4$, $BF_4$ or $PF_4$, or X and Y may form together a β-diketonate, n stands for a number of 1–3, and p and q are individually a number of 0–2, or a binuclear complex represented by the formula (4):

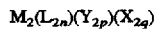
(4)

wherein M, L, X, Y, n, p and q have the same meaning as defined above.

2. A process as in claim 1, wherein the organophosphorus compound is 2,3-bis (diphenylphosphino)butane, 2,2'-bis (diphenyl)-1,1'-dinaphthyl or 2,2'-bis(ditolyphosphino)-1,1'-dinaphthyl.

3. A process as in claim 1, wherein the mononuclear complex is selected from the group consisting of [M(L)(C₂H₄)Cl], [M(L)(C₂H₄)Br], [M(L)(C₂H₄)F], [M(L)(C₂H₄)I], [M(L)(C₂H₄)CN], [M(L)(cod)]Cl, [M(L)(cod)]BF₄, [M(L)(cod)]PF₆, [M(L)(nbd)]ClO₄, [M(L)(acac)], [M(L)(pyridime)]Cl, and [M(L)(nbd)CH₃COO] wherein cod means cyclooctradiene, nbd denotes norbornadiene, and acac stands for acetylacetone.

4. A process as in claim 1, wherein the organophosphorus compound is an optically active organophosphorus compound represented by the formula (19):

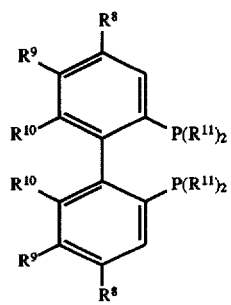
(19)

wherein $R^{11}$ means a phenyl group which may have a substituent group, $R^{10}$ is a methyl group, and $R^8$ and $R^9$ denote individually a hydrogen atom, a halogen atom or a lower alkyl group, with the proviso that $R^9$ and $R^{10}$ may form together a ring.

5. A process as in claim 4, wherein the optically active organophosphorus compound is the compound represented by the formula (22):

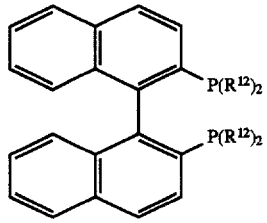
(22)

wherein $R^{12}$ means a phenyl group which may have a substituent group.

6. A process as in claim 5, wherein $R^{12}$ is a phenyl group or p-tolyl group.

7. A process as in claim 1, wherein the organophosphorus compound is an optically active organophosphorus compound which has asymmetry and is represented by the formula (20) or (21):

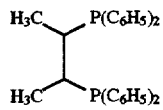
(20)

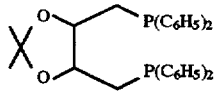
(21)

8. A process as in claim 1, wherein the transition metal-containing catalyst is selected from the group consisting of
[Rh(cod)(S)-CHIRAPHOS]ClO₄,
[Rh(cod)(R) -TolBINAP]ClO₄,
[Ru₂Cl₄((R)-BINAP)₂](NEt₃),
[Ru₂Cl₄((S)-BINAP)₂](NEt₃),
[Ru(OAc)₂(S)-TolBINAP] and
[RuI(p-cymene)(R)-TolBINAP]I
wherein cod means cyclooctadiene, Et is ethyl group, Ac is acetyl group, CHIRAPHOS means an optically active organophosphorus compound represented by the formula (20):

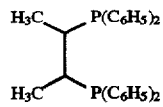
(20)

TolBINAP means an optically active organophosphorus compound represented by the formula (22):

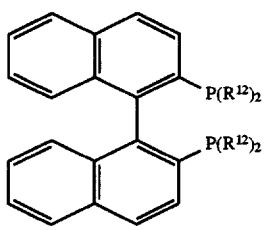

wherein $R^{12}$ is p-tolyl group, and BINAP means an optically active organophosphorus compound represented by said formula (22) wherein $R^{12}$ is a phenyl group.

9. A process as in claim 1, wherein the transition metal-containing catalyst is obtained from $[Rh(cod)_2]ClO_4$ wherein cod means cyclooctadiene and an organophosphorus compound selected from the group consisting of (2S,3S)-Bis(diphenylphosphino)butane, (2R,3R)-Bis(diphenylphosphino)butane, (R)-TolBINAP and (S)-TolBINAP wherein TolBINAP means an optically active organophosphorus compound represented by the formula (22):

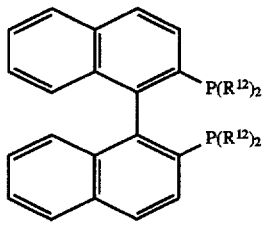

(22)

wherein $R^{12}$ is p-tolyl group.

10. A process as in claim 1, wherein the transition metal-containing catalyst is selected from the group consisting of $Ru(OAc)_2[(S)\text{-TolBINAP}]$, $Ru(OAc)_2[(R)\text{-BINAP}]$,

[RuI(p-cymene)((S)-TolBINAP)]I and

[RuI(p-cymene)((R)-TolBINAP)]I wherein Ac is an acetyl group, TolBINAP means an optically active organophosphorus compound represented by the formula (22):

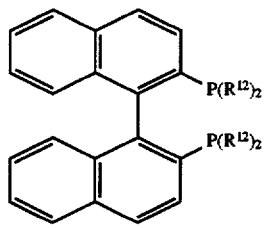

(22)

wherein $R^{12}$ is p-tolyl group, and BINAP means an optically active organophosphorus compound represented by said formula (22) wherein $R^{12}$ is a phenyl group.

* * * * *

UNITED STATES PATENT AND TRADEMARK OFFICE
CERTIFICATE OF CORRECTION

PATENT NO. : 5,631,397

DATED : May 20, 1997

INVENTOR(S) : Yamasaki, et al

It is certified that error appears in the above-identified patent and that said Letters Patent is hereby corrected as shown below:

Column 23, line 11, "$(R^5)_2P-A-P(R^3)_2$" should read --$(R^5)_2P-A-P(R^5)_2$--.

Column 23, line 62, "pyridime" should read --pyridine--.

Column 23, line 63, "cyclooctradiene" should read --cyclooctadiene--.

Signed and Sealed this

Seventh Day of October, 1997

Attest:

BRUCE LEHMAN

Attesting Officer

Commissioner of Patents and Trademarks